United States Patent [19]
Winn

[11] Patent Number: 5,800,371
[45] Date of Patent: Sep. 1, 1998

[54] SPORTSMAN'S KNEE BRACE

[75] Inventor: Michael R. Winn, San Diego, Calif.

[73] Assignee: Kevin Robbins, San Diego, Calif.; a part interest

[21] Appl. No.: 870,565

[22] Filed: Jun. 6, 1997

[51] Int. Cl.$^6$ .................................................. A61F 5/00
[52] U.S. Cl. ........................................ 602/26; 473/207
[58] Field of Search ............................. 602/5, 12, 20, 602/23, 26; 473/207, 212, 214, 266, 269, 276; 128/DIG. 15, 870, 877, 878, 881, 882

[56] References Cited

U.S. PATENT DOCUMENTS

| 3,900,199 | 8/1975 | McGonagle | 473/214 |
|---|---|---|---|
| 3,975,015 | 8/1976 | Owens et al. | 473/214 X |
| 4,088,326 | 5/1978 | Bifulco | 473/207 |
| 4,294,238 | 10/1981 | Woodford | 602/23 |
| 4,580,555 | 4/1986 | Coppess | 602/23 |
| 4,706,957 | 11/1987 | Jackson | 473/207 |
| 5,385,534 | 1/1995 | Cassford | 602/23 X |
| 5,395,117 | 3/1995 | Ogden | 473/214 X |
| 5,651,743 | 7/1997 | Stephan et al. | 473/214 X |
| 5,656,023 | 8/1997 | Caprio Jr. et al. | 602/63 |
| 5,669,873 | 9/1997 | Towsley | 602/23 X |

FOREIGN PATENT DOCUMENTS 2578416  9/1986  France .................................. 602/63

OTHER PUBLICATIONS

Edwin Watts Golf Shops 1996 Sprng Catalog Power-Coil Golf Swing Trainer Brochure, Golfswing, Inc.

Primary Examiner—Linda C. Dvorak
Attorney, Agent, or Firm—Henri J. A. Charmasson; John D. Buchaca

[57] ABSTRACT

A brace applied to the back of the knee for inducing a golf or baseball player to assume a correct swinging stance comprises a rigid, padded, oblong plate folded outwardly to an obtuse angle about a near-media transversal line, and secured to the thigh, lower knee and calf of the player by series of three straps securable at an infinity of positions along the backside of the plate.

14 Claims, 1 Drawing Sheet

U.S. Patent      Sep. 1, 1998      5,800,371
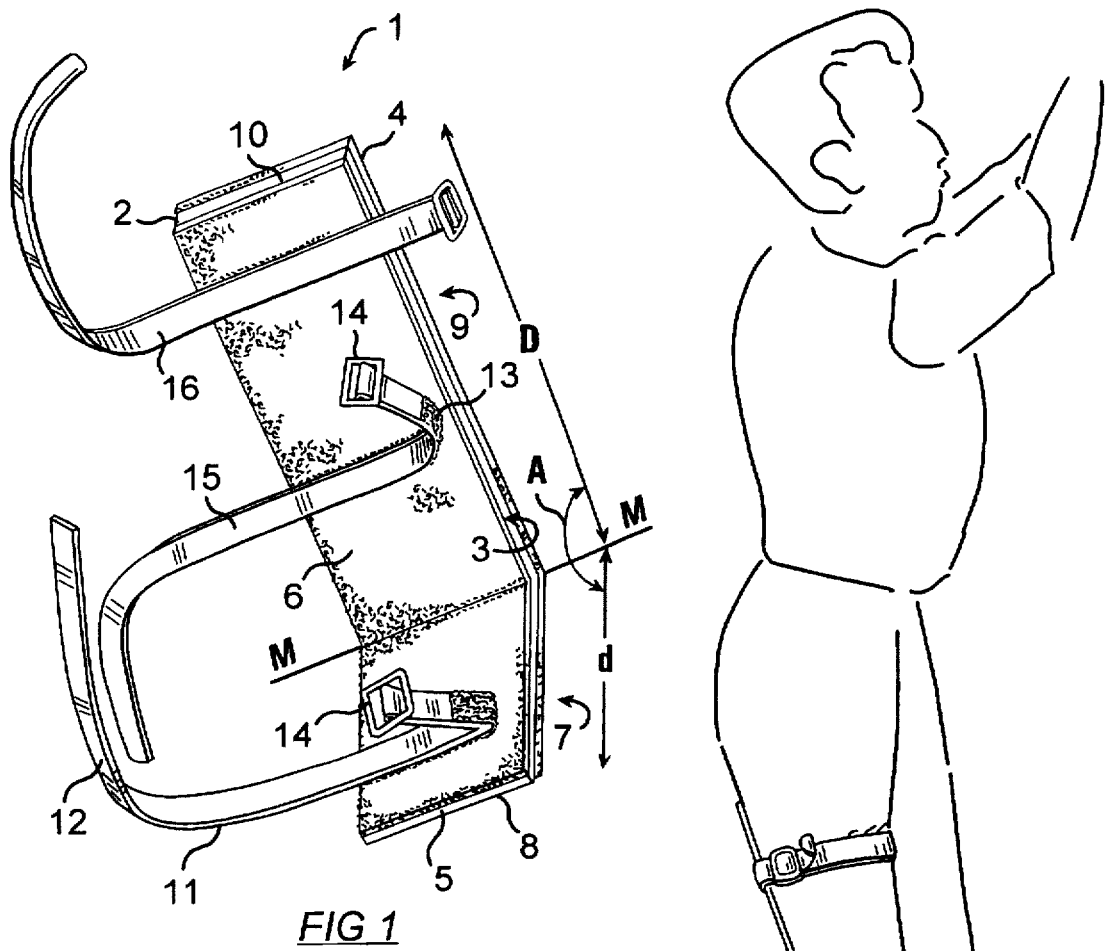
*FIG 1*
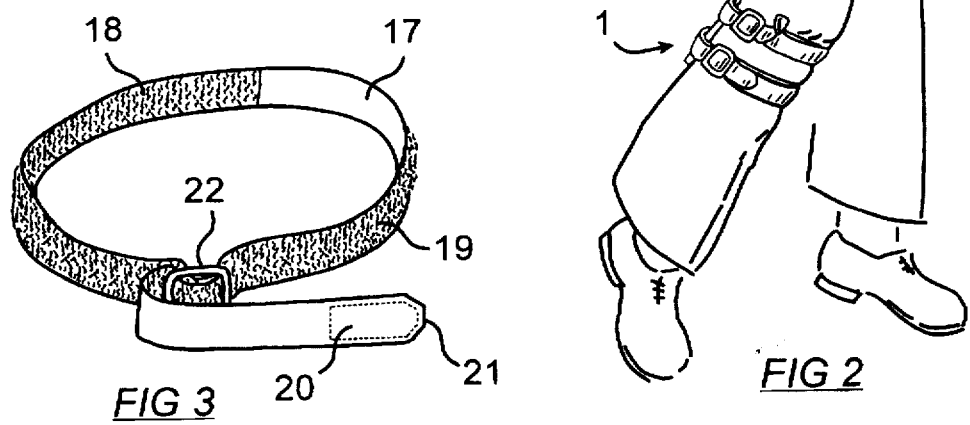
*FIG 3*
*FIG 2*

# SPORTSMAN'S KNEE BRACE

FIELD OF THE INVENTION

This invention relates to sporting goods and training aids, and more particularly to devices intended to induce a particular leg posture in the practice of a sport.

BACKGROUND OF THE INVENTION

In the game of golf, as in many other sports, including baseball, over-the-line, softball, and any other sport wherein a ball is struck by an implement swung by a person who is substantially stationary, it is important that the feet and legs be properly positioned. In particular, the right knee of a right handed player must be slightly flexed in order to maintain a proper balance during the backswing, stabilize the swinging movement, and induce the maximum swing force. The prior art discloses several attempts to create a practical knee brace for that purpose. Due to the great diversity in the players' anatomies, the braces have been made of different sizes and shapes. It is also significant that various straps which are provided for cinching the brace around the knee are usually fixedly secured to the brace and do not allow for comfortable and precise adjustment.

SUMMARY OF THE INVENTION

The principal and secondary objects of this invention are to provide a knee brace that induces the correct flexion of the player's knee during practice of golf, baseball, and other similar sports; and do so in the form of a versatile and universal brace that can be quickly and conveniently adjusted to the player's particular size and anatomy for maximum comfort.

These and other valuable objects are achieved by a knee brace where the cinching straps are adjustable in an infinity of transversal and axial positions to a slightly bent plate held in the crook of the knee.

BRIEF DESCRIPTION OF THE DRAWING

FIG. 1 is a perspective view of a knee brace according to the invention;

FIG. 2 illustrates the use of the brace by a golfer-in-training; and

FIG. 3 is a perspective view of an alternative adjustable leg strap according to the invention.

DESCRIPTION OF THE PREFERRED EMBODIMENT OF THE INVENTION

Referring now to the drawing, there is shown in FIG. 1, a knee brace 1 which is intended to be secured to the back of the knee of a golfer-in-training, as illustrated in FIG. 2 in order to induce a correct swinging posture.

The brace can also be used by a baseball player practicing batting.

The brace comprises a rigid, oblong plate 2 which has been bent along a near-median transversal line M—M to an angle A that can vary within the range of about 45 to 180 degrees depending upon the application. For typical golf, baseball or softball applications, an obtuse angle between about 91 to 170 degrees is preferred.

The inner face 3 of the plate is covered by a pad 4 made of synthetic foam or similar resilient material. The outer face 5 of the plate is almost entirely covered by a strip 6 of hook-type fabric fastener sold commercially under the brand name VELCRO, that has been permanently bonded to the plate.

The lower portion 7 of the brace between the bending transversal line M—M and the bottom edge 8 has a length d that is between approximately 50% and 100% of the length D of the upper portion 9 of the brace between the folding line M—M and the top edge 10. This corresponds to a length ratio of the upper portion to the lower portion between approximately 2:1 and 1:1. For most applications, d is most preferably between about 60% and 65% of D. 60% corresponds to a length ratio of the upper portion to the lower portion of approximately 5:3. For most adults, the length D should be between about 8 and 10 inches (about 20 cm to 25 cm). The longer upper arm promotes hip rotation during swing follow-through. Brace orientation may however be inverted for some applications such as child players.

A first strap 11 has on its inner face 12 a section of vane-type fabric fastener which cooperates with the hook-type fabric fastener bonded to the outer face of the plate to provide a detachable bond at a multitude of positions over the length of the lower portion 7. That first strap is dimensioned to wrap around the calf of the player, and comprises a buckle 14 to adjustably secure one end of the strap to the opposite end. A similar second strap 15 is provided and sized to wrap around the leg below the knee area of the player. A third similar strap 16 is positioned and dimensioned to wrap around the player's thigh.

Accordingly, each strap can be removably secured to any location on the outer face 5 either transversally, that is up and down the plate, or axially to bring the buckle 14 to the most convenient location selected by the player.

An alternative form of the strap 17 is shown in FIG. 3 having on its inner face 18 a section of vane-type fabric fastener which cooperates with the hook-type fastener on the plate. Vane-type fabric fastener is also bonded to a majority of the outer face 19 of the strap 17 to cooperate with a section 20 of hook-type fastener bonded to the outer face near the free end 21 of the strap. This arrangement allows the free end to fold back over the buckle 22 and secure against the outer face of the strap, avoiding a flapping free end and providing a stronger securing of the strap buckle against slippage.

While the preferred embodiments of the invention have been described, modifications can be made and other embodiments may be devised without departing from the spirit of the invention and the scope of the appended claims.

What is claimed is:

1. A knee brace for inducing a player's proper swinging posture in the practice of sports, said brace comprising:
   a rigid, oblong plate bent outwardly to an appropriate angle about a near-median transversal line, said plate having an inner contact face and an outer face having a first fastener surface;
   a plurality of straps shaped and dimensioned to wrap around the leg of the player, each of said straps having a second fastener surface along a portion of its length; and
   each of said second fastener surface of said straps being transversally adjustably securable to said first fastener surface of said outer face at a plurality of locations along a portion of the length of said plate.

2. The brace of claim 1 which further comprises a strip of a first type of hook-and-vane fabric fastener bonded to said outer face; and
   wherein each of said straps comprises a strip of a second type of hook-and-vane fabric fastener cooperatively interlockable with said strip of the first type.

3. The brace of claim 2, wherein said strip of said first type extends substantially over the entirety of said outer face.

4. The brace of claim 2, wherein each of said straps comprises an outer surface section covered with said strip of the second type.

5. The brace of claim 4, wherein each of said straps further comprises means for adjustably securing said strap around the player's leg.

6. The brace of claim 5, wherein said means for adjustably securing comprise a buckle.

7. The brace of claim 1, which further comprises a layer of padding material covering said inner face.

8. The brace of claim 1, wherein said angle falls within a range of about 45 and 179 degrees.

9. The brace of claim 1, wherein said angle falls within a range of about 91 to 170 degrees.

10. The brace of claim 1, wherein a first portion of said plate on one side of said transversal line is longer than the remaining second portion of said plate on the opposite side of said transversal line.

11. The brace of claim 10, wherein the length ratio of said first to said second portions is between approximately 1:1 and 2:1.

12. The brace of claim 10, wherein the length ratio of said first to said second portions is approximately 5:3.

13. The brace of claim 10, wherein the length of said first portion is between about 8 and 10 inches (20 cm and 25 cm).

14. The brace of claim 1, which further comprises means for adjustably and detachably securing a section of each of said straps axially and transversally at any location of said outer face.

* * * * *